United States Patent [19]

Riva et al.

[11] Patent Number: 4,870,195
[45] Date of Patent: Sep. 26, 1989

[54] OXIDATION CATALYST AND PROCESS FOR ITS PREPARATION

[75] Inventors: Alfredo Riva, Argelato; Fabrizio Cavani, Modena, both of Italy

[73] Assignee: Alusuisse Italia S.p.A., Milan, Italy

[21] Appl. No.: 204,035

[22] Filed: Jun. 8, 1988

Related U.S. Application Data

[62] Division of Ser. No. 110,283, Oct. 20, 1987.

[30] Foreign Application Priority Data

Oct. 20, 1986 [IT] Italy ................ 22064 A/86

[51] Int. Cl.$^4$ .......................... C07D 307/89
[52] U.S. Cl. ................................. 549/248
[58] Field of Search ........................ 549/248

[56] References Cited

U.S. PATENT DOCUMENTS

| | | | |
|---|---|---|---|
| 3,055,842 | 9/1962 | Robinson | 252/461 |
| 3,431,297 | 3/1969 | Brockhaus | 260/533 |
| 3,464,930 | 9/1969 | Friedrichsen et al. | 502/350 |
| 3,496,233 | 2/1970 | Bohemen et al. | 260/604 |
| 3,562,185 | 2/1971 | Friedrichsen et al. | 252/456 |
| 3,799,886 | 3/1974 | Felice | 252/461 |
| 3,799,888 | 3/1974 | Suvorov et al. | 252/469 |
| 3,948,807 | 4/1976 | Fuchigami et al. | 252/456 |
| 4,096,094 | 6/1978 | Blechschmitt et al. | 502/344 |
| 4,228,038 | 10/1980 | Konig | 252/461 |
| 4,397,768 | 8/1983 | Felice | 252/432 |
| 4,482,643 | 11/1984 | Harju et al. | 502/350 |
| 4,582,912 | 4/1986 | Saleh et al. | 502/350 |

FOREIGN PATENT DOCUMENTS 51-318 4/1977 Japan.
7400465 7/1974 Netherlands.

OTHER PUBLICATIONS

I. E. Wachs et al., Applied Catalysis, 15 (1985), 339 to 352.
J. Haber, Pure and Applied Chemistry, 52 (12) 1984, 1663 to 1676.
M. S. Wainwright et al., Catal. rev.-Sci., Eng., 19 (1979), 211.
A. Vejux et al., J. Solid State Chem., 23 (1978), 93.

*Primary Examiner*—Richard L. Raymond
*Attorney, Agent, or Firm*—Fisher, Christen & Sabol

[57] ABSTRACT

An oxidation catalyst formed from $V_2O_5$ and $TiO_2$ of rutile structure is obtained by a process which comprises the following stages:

(a) preparation of a solution of Ti(IV) by dissolution (partial hydrolysis) of $TiCl_4$ in an aqueous solution at a final pH below 1.0,
(b) preparation of a solution of V(IV) by heating, in order to dissolve it, solid $V_2O_5$ suspended in an aqueous oxalic acid solution,
(c) precipitation of metatitanic acid from the Ti(IV) solution at a pH not higher than 1.3,
(d) precipitation of vanadium oxide from the said V(IV) solution in the presence of the metatitanic acid obtained in (c), and
(e) separation of the precipitate, dyring and calcination thereof at an elevated temperature.

The process provides a catalyst formed from $V_2O_5$ and $TiO_2$ of rutile structure, which has a specific surface area of the order of 10 to 60 m$^2$/g, is highly active, selective and stable under conditions of catalytic oxidation, especially under the conditions of the oxidation of o-xylene to phthalic anhydride.

22 Claims, No Drawings

OXIDATION CATALYST AND PROCESS FOR ITS PREPARATION

This is a divisional of Application Ser. No. 110,283, filed on Oct. 20, 1987.

BACKGROUND OF THE INVENTION

1. Field Of The Invention

The present invention relates to an oxidation catalyst formed from $V_2O_5$ (vanadic anhydride or vanadium pentoxide) and $TiO_2$ (titanium dioxide) of rutile structure, to the process for the preparation of such a catalyst and to the use of the same catalyst in catalytic oxidation processes, especially in the process for oxidizing o-xylene to phthalic anhydride.

2. Background Art

Oxidation catalysts consisting cf vanadium and titanium oxides, which may contain an oxidation promoter, especially an alkali metal halide, are known from the state of the art.

These known catalysts can be obtained by impregnating a preformed $TiO_2$ support of rutile structure with an aqueous solution of a decomposable vanadium salt and decomposing the vanadium compound a an elevated temperature to obtain the corresponding oxide. These catalysts show in general a low activity in oxidation processes, presumably due to the low surface area of the support. In fact, the industrial preparation of rutile takes place by calcination at very high temperatures, of the order of 900° to 1,000° C., of anatase $TiO_2$ obtained by the sulfate or chloride process, add such a calcination at elevated temperatures leads to a diminution of the surface area of the rutile.

In practice, the assumption that the rutile structure of the $TiO_2$ leads to poorer characteristics for the catalyst derives essentially from the experimental evidence that the transformation of the anatase structure into the rutile structure in the catalysts formed from vanadium and titanium oxides leads to the following undesirable phenomena: a sharp decrease in the values of the surface area, destruction of the porous structure (macropores) and formation of a solid solution of $V^{4+}$ in the rutile lattice, with consequent destruction of the so-called "monolayer" of vanadium on the anatase.

These phenomena contribute to the loss of activity of the catalyst in the oxidation of o-xylene to phthalic anhydride, and it has been reported that the formation of certain percentages of rutile in the catalyst lead to a significant reduction in the useful product yield from the reaction.

It is therefore generally preferred to use catalysts formed from oxides of vanadium and titanium containing $TiO_2$ of anatase structure, and these catalysts can be obtained either by impregnation of preformed anatase with an aqueous solution of a vanadium salt or by coprecipitation of the hydrated titanium and vanadium oxides from a solution of the corresponding soluble salts, followed by drying of the precipitate thus obtained and calcination of the dried precipitate at elevated temperature.

In the technical and patent literature, the fact has been widely stressed that the catalysts for the oxidation of o-xylene to phthalic anhydride, based on $V_2O_5$ and $TiO_2$, require the anatase structure for the $TiO_2$ namely in order to obtain active and selective catalysts, and reference is made in this respect to the descriptions by: I. E. Wachs et al., Applied Catalysis, 15 (1985) 339; J. Haber, Pure and Applied Chemistry, 56 (12) (1984) 1663; M. S. Wainwright et al., Catal. Rev. - Sci. Eng., 19 (1977)( 211; and also the descriptions in U.S. Pat. Nos. 4,228,038 and 4,397,768 and 4,498,204, and German Pat. No. 1,553,728.

Various theories have been advanced to explain the need to have anatase $TiO_2$ in the catalysts under discussion, such as, for example, the presence of a crystallographic similarity between the most exposed surface planes in $TiO_2$ and the crystallographic planes of the $V_2O_5$ which contain the active and selective sites. Reference is made in this respect to the description by A. Vejux et al., J. Solid State Chem., 23 (1978) 93.

On the other hand, it must be remembered that the presence of vanadium in the catalyst favors the transformation of anatase $TiO_2$ to rutile and lowers the transformation temperature from 900° to 1,000° C. down to 500–600° C.

Therefore, in spite of accurate control of the temperature profile and the hot spots in the catalyst bed, when the catalysts based on vanadium and titanium oxides are used, a partial transformation of the anatase into rutile, with a consequent reduction in the performance of the catalyst, takes place in the course of a certain period of time.

BROAD DESCRIPTION OF THE INVENTION

It is the main object of the invention to provide a $V_2O_5$ and $TiO_2$ catalyst which, while containing $TiO_2$ in the rutile structure, overcomes the disadvantages of the analogous catalysts of the state of the art. Another object of the invention is to provide a $V_2O_5$ and $TiO_2$ catalyst which is suitable for operation at temperatures lower than those normally used in industrial oxidation processes, in particular in the oxidation of o-xylene to phthalic anhydride, while maintaining the high productivity and conversions at the industrially desirable level. A further object of the invention is therefore, to provide a catalyst of the above-mentioned type which has a longer service life. Yet another object of the invention is to provide a process for preparing a $V_2O_5$ and $TiO_2$ catalyst which allows the $TiO_2$ to be obtained directly in the rutile structure and leads therefore to a catalyst having the above mentioned advantages.

These and further objects, which become more apparent in the following text, are achieved by an oxidation catalyst, which comprises vanadium pentoxide and titanium dioxide of rutile structure, the said catalyst containing 1 to 50 percent by weight of vanadium pentoxide and having a surface area in the range from 10 to 60 $m^2/g$.

According to a further subject of the invention, the above-mentioned objects are achieved by a process for preparing an oxidation catalyst (which is described generally and in detail below) which comprises the following stages:

(a) preparation of a solution of Ti(IV) by partial hydrolysis of $TiCl_4$ in an aqueous solution at a temperature below 50° C. and a final pH below 1.0;

(b) preparation of a solution of V(IV) by dissolving, by means of heating, solid $V_2O_5$ suspended in an aqueous oxalic acid solution;

(c) precipitation of metatitanic acid from the said Ti(IV) solution, while maintaining the pH at no higher than 1.3;

(d) precipitation of vanadium oxide from the said V(IV) solution in the presence of the metatitanic acid obtained in (c); and (e) separation of the precipitate obtained in (d), drying and calcination thereof at a temperature above 300° C.

According to an embodiment of the process, which is the subject of the invention, the procedure starts with the precipitation of metatitanic acid [stage (c)] from a mixture of the Ti(IV) and V(IV) solutions prepared in (a) and (b) respectively. In this case, owing to the conditions used, which are explained in more detail below, a selective precipitation of metatitanic acid takes place in the absence or substantial absence of precipitation of the vanadium.

According to an alternative embodiment of the process of the invention, the metatitanic acid is precipitated from the Ti(IV) solution in the absence of the vanadium compound, the V(IV) solution is then added to the suspension thus obtained and, finally, the vanadium oxide is precipitated onto the metatitanic acid.

The oxidation catalyst of the invention comprises vanadium pentoxide and titanium dioxide of rutile structure, the said catalyst containing 1 to 50 percent by weight of vanadium pentoxide and having a surface area in the range from 10 to 60 m$^2$/g. Suitably the catalyst contains 10 to 20 percent by weight of vanadium pentoxide. Suitably the catalyst also contains at least one oxidation promoter selected from the group comprising potassium, rubidium, cesium, antimony, boron, phosphorus and mixtures thereof.

The process and the catalyst according to the invention are explained in more detail in the text which follows.

Stage (a)

According to the process of the invention, a Ti(IV) solution is prepared by dissolution (partial hydrolysis) of TiCl$_4$ in an aqueous hydrochloric acid solution. The final pH of the solution must be below 1.0 and is preferably about 0. The temperature during the dissolution must be maintained at values below about 50° C and preferably within the rang from 20° to 40° C.

If the temperature and pH conditions are not adhered to, total hydrolysis of TiCl$_4$ with precipitation of metatitanic acid can take place.

The hydrolysis of TiCl$_4$ can also be carried out in water, under the temperature condition indicated above, in the absence of added hydrochloric acid. In fact, liberation of hydrochloric acid takes place during the partial hydrolysis of TiCl$_4$, and this takes place during the partial hydrolysis of TiCl$_4$, and this takes the acidity to values at which redissolution of the titanic acid, which may be precipitated, can occur. Nevertheless, in this case, the Ti(IV) solution obtained is less stable in time and leads in the course of a few days to the precipitation of TiO(OH)$_2$. Instead, when operating according to the preferred embodiment in the presence of HCl, a Ti(IV) solution which is stable for several months is obtained.

Stage (b)

According to the process of the invention, a V(IV) solution is prepared by heating, in order to dissolve it, solid V$_2$O$_5$ suspended in an aqueous solution of oxalic acid. The initial molar ratio of oxalic acid and vanadium is advantageously maintained at a value in the range from 0.5/1 to 2/1, preferably about 1.5/1. In fact, an oxalic acid quantity lower than the above-mentioned ratios leads to an incomplete reduction of the vanadium and, in such a case, a step for separating off the unreduced excess V$_2$O$_5$ is necessary. A great quantity of oxalic acid can have an adverse effect in the subsequent precipitation of the metal oxides and lead to a final catalyst in which the TiO$_2$ contains a certain fraction of undesired anatase structure.

In general, the V$_2$O$_5$ suspension in the aqueous oxalic acid solution is heated to a temperature between 40° and 70° C. and, under these conditions, a complete or substantially complete reduction of V$_2$O$_5$ to V(IV) (blue solution) is achieved in a period of time from 20 minutes to about 2 hours, depending on the temperature applied.

Stage (c)

According to the process of the invention, metatitanic acid TiO(OH)$_2$ is precipitated from the solution obtained in stage (a).

According to a possible embodiment of the process, the precipitation of metatitanic acid is carried out before mixing of the aqueous solutions obtained in stages (a) and (b) in proportions depending on the desired value of the Ti/V ratio in the resulting solution, which varies from 1 to 100, and hence in the catalyst obtained at the end. The quantity of vanadium in the catalyst, expressed as a percentage by weight of V$_2$O$_5$, can in general vary from 1 percent to 50 percent and is preferably of the order of 10 to 20 percent.

Conveniently, the mixing of the solutions is carried out at ambient temperature values (20° to 25° C.) and the pH value of the resulting solution is below 1.0 and preferably is about 0.

The metatitanic acid is precipitated by addition of an alkalizing agent which takes the pH from the initial value (which is below 1.0 and preferably about zero) up to a value no higher than 1.3. The preferred alkalizing agent is ammonia, the use of which makes it possible to avoid the introduction of metallic cations into the solution. Moreover, the addition is carried out while maintaining the mixture under vigorous stirring, and preferably the alkalizing agent is added gradually in order to allow better pH control. In this treatment, an initial opalescense appears which increases progressively and finally leads to the complete or substantially complete precipitation of metatitanic acid. The precipitation temperature can vary from ambient values (20° to 25° C.) to the boiling point of the solution. Nevertheless, ambient or slightly higher temperature values are preferred. The time required for achieving complete precipitation of metatitanic acid depends essentially on the preselected temperature of the precipitation and on the final pH value, and it is generally in the range from 1 to 24 hours.

It is to be noted that the pH value during the phase of precipitating the metatitanic acid is critical. In fact, if the pH value of about 1.3 is exceeded, orthotitanic acid (Ti(OH)$_4$) is precipitated which, in the subsequent calcination treatment of the catalyst, leads to the formation of TiO$_2$ of anatase structure.

According to an alternative form of stage (c), the metatitanic acid is precipitated by thermal hydrolysis of the solution resulting from the mixing of the Ti(IV) and V(IV) solutions, operating at pH values below 1.0 and preferably around zero. In this case, the mixture of the two solutions is heated to a temperature from about 55° C. up to a temperature just below the boiling point of the mixture (about 100° C.), values of the order of 80° to 85° C. being preferred. Under these conditions, a substantially complete precipitation of metatitanic acid is achieved in a time of the order of 1 hour.

Operating under the conditions described above leads to a selective precipitation of Ti in the absence of precipitation of vanadium or at least substantial precipitation thereof, since only small traces of vanadium can remain combined with the metatitanic acid precipitate.

According to a further possible embodiment of stage (c), the metatitanic acid is precipitated from the Ti(IV) solution in the absence of the vanadium compound but following in other respects the procedure reported above. In this case, a suspension of the precipitate in the aqueous "mother" solution is obtained, to which the V(IV) solution is then added, and the mixture obtained is treated in the next stage (d) as explained below.

Stage (d)

In this stage, the vanadium oxide is precipitated in its hydrated form on the metatitanic acid either from the solution, from which the metatitanic acid was previously precipitated, or from the mixture of metatitanic acid precipitated beforehand with the V(IV solution.

For this purpose, an alkalizing agent, for example ammonia, is added to the suspension resulting from the preceding stage, in order to take the pH to a value of about 5 to cause the vanadium to precipitate in the form of hydrated oxide. Preferably, the alkalizing agent is added gradually to the suspension of metatitanic acid, with continued stirring, at a temperature from ambient (20° to 25° C.) to about 90° C.

Alternatively, the precipitation of the vanadium oxide is carried out by evaporating the solvent under atmospheric pressure or reduced pressure.

Stage (e)

The precipitate obtained in stage (d) is separated off, dried and calcined.

The drying is conveniently carried out at temperatures below about 150° C. and can be preceded by a washing of the precipitate with water.

The calcination is carried out at a temperature above 300° C. and preferably at a temperature from 380° to 500° C., for a time longer than 1 hour and preferably of the order of 5 hours.

This gives the catalyst according to the invention, formed from $V_2O_5$ and $TiO_2$, with a percentage of $V_2O_5$ of 1 percent to 50 percent by weight and preferably of the order of 10 to 20 percent, and containing $TiO_2$ of rutile structure and having a surface area of the order of 10 to 60 $m^2/g$.

The catalyst according to the invention can also contain an oxidation promoter in addition to the $V_2O_5$ and rutile $TiO_2$. Such a promoter, which can be selected from those known from the state of the art, such as, for example, phosphorus, rubidium, cesium, potassium, boron, antimony, molybdenum, tungsten and their precursors or mixtures, is added in stage (a) or (b) or in that of mixing the Ti(IV) and V(IV) solutions, in such quantities that it is present in the finished catalyst in the percentages known from the state of the art, for example within the range from 0.1 to 10 percent.

The catalyst of the invention exhibits an exceptionally high stability under oxidation conditions, is suitable for operation at temperatures lower than those normally used on the industrial scale, thus leading to high productivity and conversions, and in addition has an extended service life in the production cycle.

The said catalyst is particularly useful in the processes for the oxidation of o-xylene to phthalic anhydride.

DETAILED DESCRIPTION OF THE INVENTION

The experimental examples which follow are illustrative and do not restrict the scope of the invention.

EXAMPLE 1

10 g of $V_2O_5$ (vanadic anhydride) are suspended in a solution of $H_2C_2O_4.2H_2O$ (20.8 g in 200 $cm^3$ of distilled $H_2O$) in a three-necked glass flask; the suspension is heated, with stirring and under a nitrogen stream, to 70° C. by means of a heating jacket, until the $V_2O_5$ has been completely reduced to V(IV), that is to say until a clear blue solution is obtained. The time needed for complete reduction is about 2 hours. The solution is cooled and any unreacted residues of $V_2O_5$ are separated off by filtration. 50 $cm^3$ of $TiCl_4$ are slowly added dropwise to a second flask immersed in a water/ice bath and containing a solution of HCl in $H_2O$ (10 $cm^3$ of 37 percent HCl in 300 $cm^3$ of $H_2O$); the solution is kept under vigorous stirring during the partial hydrolysis of the $TiCl_4$.

The two solutions are then mixed while cold.

The precipitation is carried out by adding dropwise, with stirring of the solution, a solution of $NH_4OH$ (30 percent of $NH_3$) until pH 1.0 is obtained in the solution. An initial opalescense forms, and the precipitation of metatitanic acid is complete after about 12 hours. By contrast, the vanadium remains in solution and is precipitated by concentrating, the solvent being evaporated in vacuo at 60° C.

The solid obtained is dried at 80° C. for 24 hours and calcined at 400° C. for 3 hours. The surface area of the catalyst obtained in the end is 45 $m^2/g$. The $TiO_2$ obtained is in the rutile crystal form, and the fraction of vanadium in the catalyst is 21.9 percent, expressed as percent by weight of $V_2O_5$.

EXAMPLE 2

The V(IV) and Ti(IV) solutions are prepared in a manner analogous to that described in Example 1. By contrast, the precipitation is carried out by heating the mixture of the two solutions to 85° C., with stirring. The hydrolysis with precipitation of metatitanic acid is complete after about 3 hours. The vanadium which, however, remains in solution is precipitated in the same solution by concentrating, the solvent being evaporated in vacuo at 60° C. The precipitate is dried at 80° C. for 24 hours and calcined at 400° C. for 3 hours.

EXAMPLES 3 to 5

The catalyst is prepared as in Example 2, but the solid product after drying is calcined at 450° C. for 3 hours, or at 500° C. for 3 hours or at 550° C. for 3 hours. The surface areas obtained are 30 $m^2/g$, 20 $m^2/g$, 14 $m^2/g$ in these three cases, respectively.

EXAMPLE 6

The catalyst is prepared analogously to Example 2, except that the initial quantity of $V_2O_5$ used for preparing the V(IV) solution is 5.0 g. The final vanadium content after calcination at 400° C. for 3 hours is 12.3 percent by weight, expressed as $V_2O_5$. The surface area is 45 $m_2/g$, and the $TiO_2$ is in the rutile crystal form.

EXAMPLE 7

The V(IV) and Ti(IV) solutions are prepared as indicated in Example 1; $NH_4OH$ (30 percent of $NH_3$) is then added dropwise up to pH 1.0 to the Ti(IV) solution, with stirring.

An initial opalescence forms, and the precipitation of metatitanic acid is complete after about 12 hours. The V(IV) solution is then added with stirring to the suspension; vanadium oxide then precipitates in its hydrated form when the solvent is evaporated in vacuo at 60° C.

The treatment of the precipitate is analogous to that indicated in Example 1. After calcination, the catalyst shows the rutile structure of $TiO_2$, has a surface area of 45 $m^2/g$ and a vanadium content of 21.9 percent expressed as percent by weight of $V_2O_5$.

EXAMPLE 8

The V(IV) and Ti(IV) solutions are prepared in a manner analogous to that reported in Example 1; the Ti(IV) solution is heated to 85° C., with stirring; the hydrolysis with precipitation of metatitanic acid is complete after about 2 hours. The V(IV) solution is then added with stirring to the suspension; the vanadium oxide then precipitates in its hydrated form, when the solvent is evaporated in vacuo at 60° C.

The treatment of the precipitate is analogous to that indicated in Example 1. After calcination, the catalyst shows the rutile structure of $TiO_2$, has a surface area of 45 $m^2/g$ and a vanadium content of 21.9 percent, expressed as percent by weight of $V_2O_5$.

EXAMPLE 9

The preparation procedure is analogous to that reported in Example 7, but the metatitanic acid, once the precipitation is complete, is filtered off and the solid residue is washed with $H_2O$, dried at 80° C. for 24 hours and then calcined at 400° C. for 3 hours. This gives $TiO_2$ in the rutile crystal form with a surface area of 40 $m^2/g$. The solid is then suspended in the V(VI) solution; the vanadium is precipitated in its hydrated form, when the solvent is evaporated in vacuo at 60° C. The precipitate is dried at 80° C. for 24 hours and calcined at 400° C. for 3 hours.

EXAMPLE 10

The preparation procedure is analogous to that reported in Example 8, but the metatitanic acid, once. precipitation is complete, is filtered off and the solid residue is washed with $H_2O$, dried at 80° C. for 24 hours and then calcined at 400° C. for 3 hours. This gives $TiO_2$ in the rutile crystal form with a surface area of 40 $m^2/g$. The solid is suspended in the V(IV) solution; the vanadium is precipitated in its hydrated form, when the solvent is evaporated in vacuo at 60° C. The precipitate is dried at 80° C., for 24 hours and calcined at 400° C. for 3 hours.

EXAMPLES 11 to 14

The preparation procedure is analogous to that reported in Examples 7 to 10, except that the V(IV) solution is prepared by reduction of 5.0 g of $V_2O_5$. The catalysts finally obtained contain 12.3 percent by weight of $V_2O_5$.

EXAMPLES 15 to 17

The catalysts prepared by the procedure reported in the preceding examples are used for the gas-phase oxidation with air of o-xylene to phthalic anhydride.

The process is run at temperatures in the range from 290° to 330° C., that is to say lower than the temperatures 360° to 380° C. which can be used with commercial catalysts, and at high hourly space velocities of the gas of the order of about 5,000 hours $^{-1}$, o-xylene conversions of about 99 percent and higher being obtained.

These data precisely demonstrate the superiority of the catalysts which are the subject of the present invention and which show high activities at temperatures about 30° to 90° C. lower than those used according to the state of the art, and at space velocities much higher than the usual ones, which leads to a superior productivity and longer life of the catalyst.

What is claimed is:

1. Process comprising oxidizing o-xylene to phthalic anhydride in the presence of an oxidation catalyst comprising vanadium pentoxide, titanium dioxide of rutile structure, and an oxidation promoter selected from the group consisting of (i) potassium, (ii) rubidium, (iii) cesium, (iv) antimony, (v) boron, (vi) mixtures of oxidation promoters (i) to (v), the vanadium pentoxide or vanadium pentoxide precursor has been precipitated upon precipitated titanium precursor said catalyst containing 1 to 50 percent by weight of said vanadium pentoxide and having a surface area in the range from 10 to 60 $m^2/g$.

2. The process as claimed in claim 1 wherein the oxidation catalyst contains 10 to 20 percent by weight of the vanadium pentoxide.

3. The process as claimed in claim 1 wherein the oxidation catalyst contains 0.1 to 10 percent by weight of the oxidation promoter.

4. Process comprising oxidizing o-xylene to phthalic anhydride in the presence of an oxidation catalyst comprising vanadium pentoxide, titanium dioxide of rutile structure, and an oxidation promoter selected from the group consisting of (i) potassium, (ii) rubidium, (iii) cesium, (iv) antimony, (v) boron and (vi) mixtures of oxidation promoters (i) to (v), said oxidation catalyst containing 1 to 50 percent by weight of said vanadium pentoxide and having a surface area in the range from 10 to 60 $m^2/g$, said oxidation catalysts being prepared by a process comprising the following steps:
    (a) preparation of a solution of Ti(IV) by partial hydrolysis of $TiCl_4$ in an aqueous solution at temperature below 50° C. and a final pH below 1.0;
    (b) preparation of a solution V(VI) by dissolving, by means of heating, solid $V_2O_5$ suspended in an aqueous oxalic action solution;
    (c) precipitation of a metatitanic acid from the said Ti(IV) solution, while maintaining the pH at no higher than 1.3;
    (d) precipitation of vanadium oxide from the said V(IV) solution in the presence of the metatitanic acid obtained in (c); and
    (e) separation of the precipitate obtained in (d), drying and calcination thereof at a temperature above 300° C, said oxidation promoter being added in one of stages (a), (b) or the mixing of the Ti(IV) and V(IV) solutions before stage (c).

5. The process was claimed in claim 4 wherein the partial hydrolysis stage (a) is carried out in an aqueous hydrochloric acid solution to a final pH of 0.

6. The process as claimed in claim 4 wherein the partial hydrolysis stage (a) is carried out in water in the absence of added acid.

7. The process as claimed in claim 4 wherein the oxidation catalyst contains 10 to 20 percent by weight of the vanadium pentoxide.

8. The process as claimed in claim 4 wherein the oxidation catalyst contains 0.1 to 10 percent by weight of the oxidation promoter.

9. Process comprising oxidizing o-xylene to phthalic anhydride in the presence of an oxidation catalyst consisting of vanadium pentoxide and titanium dioxide of rutile structure the vanadium pentoxide or vanadium pentoxide precursor has been precipitated upon precipitated titanium precursor said catalyst containing 1 to 50 percent by weight of said vanadium pentoxide and having a surface area in the range from 10 to 60 $m^2/g$.

10. The process as claimed in claim 9 wherein the oxidation catalyst contains 10 to 20 percent by weight of the vanadium pentoxide.

11. Process comprising oxidizing o-xylene to phthalic anhydride in the presence of an oxidation catalyst consisting of vanadium pentoxide and titanium dioxide of rutile structure, said oxidation catalyst containing 1 to 50 percent by weight of said vanadium pentoxide and having a surface area in the range from 10 to 60 $m^2/g$, said oxidation catalysts being prepared by a process comprising the following steps:
  (a) preparation of a solution of Ti(IV) by partial hydrolysis of $TiCl_4$ in an aqueous solution at a temperature below 50° C. and a final pH below 1.0;
  (b) preparation of a solution V(IV) by dissolving, by means of heating, solid $V_2O_5$ suspended in an aqueous oxalic action solution;
  (c) precipitation of a metatitanic acid from the said Ti(IV) solution, while maintaining the pH at no higher than 1.3;
  (d) precipitation of vanadium oxide from the said V(IV) solution in the presence of the metatitanic acid obtained in (c); and
  (e) separation of the precipitate obtained in (d), drying and calcination thereof at a temperature above 300° C.

12. The process was claimed in claim 11 wherein the partial hydrolysis stage (a) is carried out in an aqueous hydrochloric acid solution to a final pH of 0.

13. The process as claimed in claim 11 wherein the partial hydrolysis stage (a) is carried out in water in the absence of added acid.

14. The process as claimed in claim 11 wherein the oxidation catalyst contains 10 to 20 percent by weight of the vanadium pentoxide.

15. The process as claimed in claim 1 wherein the catalytic process is conducted at a temperature below 360° C.

16. The process as claimed in claim 1 wherein the catalytic process is conducted at a temperature lower than the temperature normally used in industrial oxidation processes.

17. The process as claimed in claim 4 wherein the catalytic process is conducted at a temperature below 360° C.

18. The process as claimed in claim 4 wherein the catalytic process is conducted at a temperature lower than the temperatures normally used in industrial oxidation processes.

19. The process as claimed in claim 9 wherein the catalytic process is conducted at a temperature below 360° C.

20. The process as claimed in claim 9 wherein the catalytic process is conducted at a temperature lower than the temperatures normally used in industrial oxidation processes.

21. The process as claimed in claim 11 wherein the catalytic process is conducted at a temperature below 360° C.

22. The process as claimed in claim 11 wherein the catalytic process is conducted at a temperature lower than the temperatures normally used in industrial oxidation processes.

* * * * *